(12) United States Patent
Or-Bach

(10) Patent No.: US 11,808,878 B2
(45) Date of Patent: *Nov. 7, 2023

(54) ELECTROMAGNETIC WAVE MEDICAL IMAGING SYSTEM, DEVICE AND METHODS

(71) Applicant: Or-Ment LLC, San Jose, CA (US)

(72) Inventor: Zvi Or-Bach, Haifa (IL)

(73) Assignee: Or-Ment LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,707

(22) Filed: Feb. 9, 2023

(65) Prior Publication Data
US 2023/0273294 A1 Aug. 31, 2023

Related U.S. Application Data

(63) Continuation-in-part of application No. 17/876,531, filed on Jul. 29, 2022, which is a continuation-in-part (Continued)

(51) Int. Cl.
| | | |
|---|---|---|
| *G01S 7/02* | (2006.01) | |
| *A61B 5/0507* | (2021.01) | |
| *G01S 13/00* | (2006.01) | |
| *G01S 7/03* | (2006.01) | |
| *G01S 13/89* | (2006.01) | |

(52) U.S. Cl.
CPC ............ *G01S 7/026* (2013.01); *A61B 5/0507* (2013.01); *G01S 7/03* (2013.01); *G01S 13/89* (2013.01)

(58) Field of Classification Search
CPC ...... H01Q 21/20; H01Q 21/065; H01Q 13/20; H01Q 25/04; H01Q 15/22; H01Q 15/0006; H01Q 15/0053; H01Q 15/0086; H04B 10/2581; G01S 7/03; G01S 7/024;
(Continued)

(56) References Cited

U.S. PATENT DOCUMENTS

| | | | | |
|---|---|---|---|---|
| 3,568,190 A | * | 3/1971 | Wong | G01S 13/4409 |
| | | | | 342/149 |
| 4,527,161 A | * | 7/1985 | Wehner | G01S 13/24 |
| | | | | 342/152 |

(Continued)

*Primary Examiner* — Vladimir Magloire
*Assistant Examiner* — Michael W Justice
(74) *Attorney, Agent, or Firm* — Patent PC; Bao Tran

(57) ABSTRACT

An electromagnetic wave medical imaging system, the system including: at least one antenna; transmission electronics; receiving electronics; and receiving computing electronics, where the transmission electronics are structured to transmit a first electromagnetic wave having an Orbital Angular Momentum wave-front thru the antenna towards a target, where the transmission electronics are structured to transmit a second electromagnetic wave having a non Orbital Angular Momentum wave-front thru a first portion of the antenna towards the target, where the receiving electronics are structured to form a first signal from a first return wave of the first electromagnetic wave, where the receiving electronics are structured to form a second signal from a second return wave of the second electromagnetic wave, and where the system is designed to operate at a near field electromagnetic wave. Included are methods for operating a super resolution system.

20 Claims, 8 Drawing Sheets

Related U.S. Application Data of application No. 16/511,241, filed on Jul. 15, 2019, now Pat. No. 11,435,472.

(60) Provisional application No. 63/409,779, filed on Sep. 24, 2022, provisional application No. 62/717,895, filed on Aug. 12, 2018, provisional application No. 62/714,750, filed on Aug. 5, 2018, provisional application No. 62/698,974, filed on Jul. 17, 2018, provisional application No. 62/698,286, filed on Jul. 16, 2018.

(58) Field of Classification Search
CPC ........ G01S 7/026; G01S 13/89; G01S 13/426; A61B 5/0507
USPC ............... 343/772, 834, 836, 853, 912, 833; 702/143, 343, 853, 772, 342, 179; 342/179
See application file for complete search history.

(56) References Cited

U.S. PATENT DOCUMENTS

| | | | | |
|---|---|---|---|---|
| 5,170,171 A * | 12/1992 | Brown | ................ | G01S 13/87 342/25 C |
| 6,597,304 B2 * | 7/2003 | Fienup | ................ | G01S 7/4004 342/25 R |
| 7,583,221 B2 * | 9/2009 | Detlefsen | ................ | G01S 13/87 342/25 A |
| 7,619,554 B2 * | 11/2009 | Shklarsky | ............ | G01S 13/003 342/191 |
| 7,969,281 B2 * | 6/2011 | Kofman | ................ | G06K 19/086 340/572.1 |
| 9,031,151 B1 * | 5/2015 | Harris | ................ | H04B 7/0617 375/267 |
| 9,188,670 B2 * | 11/2015 | Bruyere | ................ | H01Q 21/061 |
| 9,250,185 B2 * | 2/2016 | Sirat | ................ | G02B 21/0076 |
| 9,413,448 B2 * | 8/2016 | Ashrafi | ............ | H04B 10/25752 |
| 9,831,561 B2 * | 11/2017 | Byun | ................ | H01Q 19/185 |
| 9,998,187 B2 * | 6/2018 | Ashrafi | ................ | H04B 7/0469 |
| 10,014,948 B2 * | 7/2018 | Ashrafi | ................ | H04L 27/36 |
| 10,153,845 B2 * | 12/2018 | Ashrafi | ................ | H04L 63/06 |
| 10,168,501 B2 * | 1/2019 | Ashrafi | ................ | G02B 6/4246 |
| 10,665,955 B2 * | 5/2020 | Hirabe | ................ | H01Q 19/17 |
| 10,761,184 B2 * | 9/2020 | Greenberg | ............ | G01S 7/411 |
| 11,245,486 B2 * | 2/2022 | Ashrafi | ................ | H04J 14/00 |
| 2003/0020648 A1 * | 1/2003 | Fienup | ................ | H01Q 3/267 342/194 |
| 2007/0293752 A1 * | 12/2007 | Simpkin | ................ | A61B 5/442 600/407 |
| 2008/0174476 A1 * | 7/2008 | Detlefsen | ............ | G01S 13/887 342/25 A |
| 2009/0231104 A1 * | 9/2009 | Kofman | ................ | G01S 13/751 340/10.1 |
| 2013/0027774 A1 * | 1/2013 | Bovino | ................ | G02B 26/0858 359/485.01 |
| 2015/0268340 A1 * | 9/2015 | Bruyere | ................ | G01S 13/9023 342/25 C |
| 2015/0357710 A1 * | 12/2015 | Li | ................ | H01Q 21/065 342/174 |
| 2016/0043794 A1 * | 2/2016 | Ashrafi | ................ | H04L 27/2017 370/329 |
| 2016/0127073 A1 * | 5/2016 | Ashrafi | ................ | H04B 10/516 398/44 |
| 2016/0315395 A1 * | 10/2016 | Byun | ................ | H01Q 19/185 |
| 2017/0026095 A1 * | 1/2017 | Ashrafi | ................ | H04B 7/10 |
| 2017/0343750 A1 * | 11/2017 | Ashrafi | ................ | H04J 14/04 |
| 2018/0262243 A1 * | 9/2018 | Ashrafi | ................ | H04B 7/10 |
| 2018/0287262 A1 * | 10/2018 | Patri | ................ | H01Q 13/02 |
| 2018/0287263 A1 * | 10/2018 | Hirabe | ................ | H01Q 19/19 |
| 2019/0041493 A1 * | 2/2019 | Greenberg | ............ | G01S 7/411 |

\* cited by examiner (a) Wavefront of mode 0. (b) Wavefront of mode 1. (c) Wavefront of mode 2. (d) Wavefront of mode 3.

(f) 3D profile of mode 1.

(e) 3D profile of mode 0.

(h) 3D profile of mode 3

(g) 3D profile of mode 2.

Wavefront and 3D profile for OAM waves with different modes.

(a) Spiral Phase Plate (SPP) antenna. (b) Uniform Circular Array (UCA) antenna. (c) Metasurface.

Three kinds of antenna structures for radio vortex signal generation.

ELECTROMAGNETIC WAVE MEDICAL IMAGING SYSTEM, DEVICE AND METHODS

BACKGROUND OF THE INVENTION

1. Field of the Invention

This application relates to the general field of RF and Radar technology and devices, and more particularly to sensing technology for self-driving cars and many other applications.

2. Discussion of Background Art

RADAR is an attractive sensing technology for self-driving cars and many other applications. Yet, the limited resolution of RADAR technologies forces many to use a far more expensive technology—LiDAR.

The resolution of Electro Magnetic ('EM') imaging is defined by the diffraction limit (diameter of the first null of the Airy disk, d/2=1.22 λN, where λ is the wavelength of the light, D is the diameter of the microscope aperture and N is the f number), also known as Rayleigh's Limit.

For microscopy advanced applications a company named BioAxial (http://www.bioaxial.com/) developed solutions leveraging the physics associated with circular polarization. The Bioaxial concept is presented in at least U.S. Pat. No. 9,250,185, and in a paper by Fallet, Clément, et al. "Conical diffraction as a versatile building block to implement new imaging modalities for superresolution in fluorescence microscopy." *Nanoimaging and Nanospectroscopy II*. Vol. 9169. International Society for Optics and Photonics, 2014, both incorporated herein by reference. Recent work discovered that the same fundamental physics affects EM and are known as Orbital Angular Momentum ("OAM") in which the center of the radiated beam, also called vertex, would have zero energy, as also referred to as singularity or null. As presented in papers by Bliokh, Konstantin Yu, et al., "Singular polarimetry: Evolution of polarization singularities in electromagnetic waves propagating in a weakly anisotropic medium." *Optics express* 16.2 (2008): 695-709; and Thidé, Bo, et al., "Utilization of photon orbital angular momentum in the low-frequency radio domain." *Physical review letters* 99.8 (2007): 087701 both incorporated herein by reference. As dark has no diffraction limit this physics could be leveraged to build a Super Resolution RADAR ('SRR'). Some work toward such a goal was reported in papers by: Chen, Yiling, et al., "Single-frequency computational imaging using OAM-carrying electromagnetic wave." *Journal of Applied Physics* 121.18 (2017): 184506; by Liu, Kang, et al., "Orbital-angular-momentum-based electromagnetic vortex imaging." *IEEE Antennas Wireless Propag. Lett.* 14 (2015): 711-714; by Liu, Kang, et al., "Study on the theory and method of vortex-electromagnetic-wave-based radar imaging." *IET Microwaves, Antennas & Propagation* 10.9 (2016): 961-968; by Liu, Kang, et al., "High-resolution electromagnetic vortex imaging based on sparse Bayesian learning." *IEEE Sensors Journal* 17.21 (2017): 6918-6927; by Yuan, Tiezhu, et al., "Radar imaging using electromagnetic wave carrying orbital angular momentum." *Journal of Electronic Imaging* 26.2 (2017): 023016; by Liu, Kang, et al., "Super-resolution radar imaging based on experimental OAM beams." *Applied Physics Letters* 110.16 (2017): 164102 by Liu, Kang, et al., "Microwave imaging of spinning object using orbital angular momentum." *Journal of Applied Physics* 122.12 (2017): 124903; by Li, Lianlin, and Fang Li. "Beating the Rayleigh limit: Orbital-angular-momentum-based super-resolution diffraction tomography." *Physical Review E* 88.3 (2013): 033205; by Yang, Taoli, et al., "Three dimensional SAR imaging based on vortex electromagnetic waves." *Remote Sensing Letters* 9.4 (2018): 343-352; by Ding, Chenliang, Jingsong Wei, and Mufei Xiao, "Super-resolution imaging based on the temperature-dependent electron-phonon collision frequency effect of metal thin films." *Journal of Applied Physics* 123.17 (2018): 174306; by Lin, Mingtuan, et al., "Super-resolution orbital angular momentum based radar targets detection." *Electronics Letters* 52.13 (2016): 1168-1170; by Bu, Xiangxi, et al., "Implementation of Vortex Electromagnetic Waves High-Resolution Synthetic Aperture Radar Imaging." *IEEE Antennas and Wireless Propagation Letters* 17.5 (2018): 764-767; and by Yuan, Tiezhu, et al., "Electromagnetic Vortex-Based Radar Imaging Using a Single Receiving Antenna: Theory and Experimental Results." *Sensors* 17.3 (2017): 630; all are incorporated herein by reference.

There is a need in the area to provide a useful application of the above scientific endeavors.

This application incorporates by reference herein the entire contents of the following: U.S. Patent Provisional Applications 62/698,286, 62/698,974, 62/714,750, and 62/717,895; and U.S. patent application Ser. Nos. 16/511,241 and 17/876,531; and U.S. Pat. No. 11,435,472.

SUMMARY

Various embodiments of the invention relate to the transmission of Circularly-Polarized OAM Radio Beams. Such a beam is called a Vortex beam having an on-axis singular-phase null region in which there is no EM energy. As an example, in a paper by Bai, Xu-Dong, et al., "Experimental array for generating dual circularly-polarized dual-mode OAM radio beams." *Scientific reports* 7 (2017): 40099, incorporated herein by reference, an antenna for forming such a beam is presented. A RADAR beam using an OAM beam should have zero return energy from the center of the wave. The technique presented herein suggests radiating twice (or more), once with a beam that carries such a 'dark spot' and once again with a beam that does not carry this 'dark spot', beam portion having zero return energy. Comparing the reflected EM waves of the two cases could enable construction of an image of/from the subject related to the dark spot location.

Radio Vortex Signal Generation antenna structures are presented in a paper by Cheng, Wenchi, et al., "Orbital angular momentum for wireless communications." arXiv preprint arXiv: 1804.07442 (2018), incorporated herein by reference. The following is from the paper: OAM is one basic physical property of an EM wave. It describes the orbital property for EM rotational degree of freedom and rotation characteristic for energy. OAM is interpreted as a beam with a number of OAM-modes which can theoretically take not only any integer value but also any non-integer value. Inherently, the EM wave carried OAM can be generated by PE wave with one phase rotation factor $\exp(il\phi)$, where $i=\sqrt{-1}$, 1 is the order/index of OAM-mode, and DRAFT Apr. 23, 2018 3 $\phi$ is the azimuthal angle (defined as the angular position on a plane perpendicular to the axis of propagation). A pure OAM-mode is characterized by integer and different OAM-modes are orthogonal with each other. When the OAM-mode is a non-integer, the phase term $\exp(il\phi)$ can be expressed by the sum of Fourier series of orthogonal OAM-modes. Affected by the rotation phase factor, the wavefront phase is a spiral structure instead of a planar structure. The wavefront phase rotates around the beam propagation direction and the phase changes 2πd after a full turn. FIG. 1A shows the wavefront and 3 dimensional (3D) profile for OAM waves with different modes, where the transmit antenna is uniform circular array (UCA) antenna with 16 array-elements. FIGS. 1A (a)-1(d) show the wavefront phase corresponding to OAM-modes 0, 1, 2, and 3, respectively. In fact, OAM-mode 0 represents the PE wave as shown in FIG. 1A (a). Based on FIGS. 1A (a)-1(d), we can observe that the spiral characteristic of OAM wave becomes complicated and the phase changes sharply as the order/index of OAM-modes increases within the same distance. FIGS. 1A (e)-1(h) show the 3D profiles of OAM waves for different OAM-modes 0, 1, 2, and 3, respectively. There exist central hollow for different OAM-modes except OAM-mode 0. This is because the OAM wave of mode 0 is in fact the PE wave. The central hollow increases as the order of OAM-mode increases. Also, the power gain decreases as the order of OAM-mode increases. This indicates that it is impossible for long distance OAM wave transmission by directly using OAM-modes. For long distance transmission, we need to converge the hollow OAM wave.

Different from traditional PE wave based signals, radio vortex signals have the phase rotation factor exp(ilφ). There are some popular facilities can be used to generate radio vortex signal such as Spiral Phase Plate (SPP) antenna, Uniform Circular Array (UCA) antenna, and metasurfaces, as shown in FIG. 1B.

SPP antenna [as presented at a paper by Y. Ren, L. Li, G. Xie, Y. Yan, Y. Cao, H. Huang, N. Ahmed, Z. Zhao, P. Liao, C. Zhang, G. Caire, A. F. Molisch, M. Tur, and A. E. Willner, "Line-of-sight millimeter-wave communications using orbital angular momentum multiplexing combined with conventional spatial multiplexing," IEEE Transactions on Wireless Communications, vol. 16, no. 5, pp. 3151-3161, May 2017, incorporated herein by reference]: An example of SPP antenna is given in FIG. 1B (a). The SPP antenna generates the phase delay by increasing the antenna thickness in proportion to the azimuthal angle or by drilling inhomogeneous holes in a dielectric plate to change the equivalent permittivity. The SPP antenna has the advantages of small divergence and low attenuation as well as the disadvantages of not being applicable for relatively low frequency transmission and cannot generate multiple OAM-modes simultaneously.

UCA antenna [as presented at a paper by M. Lin, Y. Gao, P. Liu, and J. Liu, "Theoretical analyses and design of circular array to generate orbital angular momentum," IEEE Transactions on Antennas and Propagation, vol. 65, no. 7, pp. 3510-3519, July 2017, incorporated herein by reference]: An example of UCA antenna is given in FIG. 1B (b). The phase information of adjacent array-element of UCA antenna is linearly increased by 2πl/N, where N is the Apr. 23, 2018 DRAFT 6 number of array-elements. The UCA antennas are low profile, low weight, and easy to manufacture with rectangular patch arrays. Also, the UCA antennas can simultaneously generate multiple vortex beams with multiple OAM-modes even in the radio frequency band. However, the vortex beams generated by UCA are divergent and centrally hollow. Thus, the UCA antennas need to be jointly used with the converging schemes to combat the signal attenuation during the propagation.

Metasurfaces [as presented at a paper by S. Yu, L. Li, G. Shi, C. Zhu, X. Zhou, and Y. Shi, "Design, fabrication, and measurement of reflective metasurface for orbital angular momentum vortex wave in radio frequency domain," Applied Physics Letters, vol. 108, no. 12, pp. 5448, 2016, incorporated herein by reference]: An example of metasurfaces is given in FIG. 1B (c). In the metasurfaces based OAM signal generation schemes, the wavefront of electromagnetic waves are controlled by regulating phase shift to the incoming waves. These schemes have the advantages of low profile, small mass, and low manufacturing cost. However, it is hard to accurately control the phase for signal modulation and thus not applicable to multiple OAM-modes transmission in wireless communications.

Herein techniques utilizing this concept are presented to enable a Super Resolution RADAR (SRR), and applications for such an SRR are presented.

In one aspect, a super resolution radar system, the radar system comprising: at least one antenna; transmission electronics; receiving electronics; and receiving computing electronics, wherein said transmission electronics is structured to transmit a first electromagnetic wave having an Orbital Angular Momentum wave-front using said antenna, wherein said transmission electronics is structured to transmit a second electromagnetic wave having a no Orbital Angular Momentum wave-front using a first portion of said antenna, wherein said receiving electronics is structured to form a first signal from a first return wave of said first electromagnetic wave, wherein said receiving electronics is structured to form a second signal from a second return wave of said second electromagnetic wave, and wherein said receiving computing electronics is structured to subtract said first signal from said second signal.

In another aspect, a method for operating a super resolution radar, the method comprising: providing a supper resolution radar system comprising at least one antenna, transmission electronics, receiving electronics and receiving computing electronics; forming a first electromagnetic wave comprising an Orbital Angular Momentum wave-front, wherein said transmission electronics is used to form said first electromagnetic wave; transmitting said first electromagnetic wave using said antenna; forming a second electromagnetic wave comprising a no Orbital Angular Momentum wave-front, wherein said transmission electronics is used to form said second electromagnetic wave; transmitting said second electromagnetic wave using a first portion of said antenna, receiving a first return wave of said first electromagnetic wave; processing said first return wave to form a first signal; receiving a second return wave of said second electromagnetic wave; processing said second return wave to form a second signal, wherein said processing is performed by said receiving electronics; and subtracting said first signal from said second signal, wherein said subtracting is performed by said receiving computing electronics.

In another aspect, a super resolution radar system, the radar system comprising: at least one antenna; transmission electronics; receiving electronics; and receiving computing electronics, wherein said antenna is a circular array type comprising at least four leaves, wherein said transmission electronics is structured to transmit a first electromagnetic wave using all leaves of said antenna, wherein said transmission electronics is structured to transmit a second electromagnetic wave, wherein said transmit a second electromagnetic wave comprises at least one leaf of said antenna not used, wherein said receiving electronics is structured to form a first signal from a first return wave of said first electromagnetic wave, wherein said receiving electronics is structured to form a second signal from a second return wave of said second electromagnetic wave, and wherein said receiving computing electronics is structured to subtract said first signal from said second signal.

In another aspect, a super resolution system, the system comprising: at least one antenna; transmission electronics; receiving electronics; and receiving computing electronics, wherein said transmission electronics are structured to transmit a first electromagnetic wave having an Orbital Angular Momentum wave-front thru said antenna towards a target, wherein said transmission electronics are structured to transmit a second electromagnetic wave having a non Orbital Angular Momentum wave-front thru a first portion of said antenna towards said target, wherein said receiving electronics are structured to form a first signal from a first return wave of said first electromagnetic wave, wherein said receiving electronics are structured to form a second signal from a second return wave of said second electromagnetic wave, and wherein said receiving computing electronics are structured to compute target information by using at least one difference between said first signal and said second signal.

In another aspect, a super resolution system, the system comprising: at least one antenna; transmission electronics; receiving electronics; and receiving computing electronics, wherein said transmission electronics are structured to transmit a first electromagnetic wave having a non Orbital Angular Momentum wave-front thru a first portion of said antenna towards a target, wherein said transmission electronics are structured to transmit a second electromagnetic wave having an Orbital Angular Momentum wave-front thru said antenna towards said target, wherein said receiving electronics are structured to form a first signal from a first return wave of said first electromagnetic wave, wherein said receiving electronics are structured to form a second signal from a second return wave of said second electromagnetic wave, and wherein said receiving computing electronics are structured to compute target information by using at least one difference between said first signal and said second signal.

In another aspect, a method for operating a super resolution system, the method comprising: providing a super resolution system comprising at least one antenna, transmission electronics, receiving electronics, and receiving computing electronics; forming a first electromagnetic wave comprising an Orbital Angular Momentum wave-front, wherein said transmission electronics are used to form said first electromagnetic wave; transmitting said first electromagnetic wave using said antenna; forming a second electromagnetic wave comprising a non Orbital Angular Momentum wave-front, wherein said transmission electronics are used to form said second electromagnetic wave; transmitting said second electromagnetic wave using a first portion of said antenna; receiving a first return wave comprising said first electromagnetic wave; processing said first return wave to form a first signal; receiving a second return wave comprising said second electromagnetic wave; processing said second return wave to form a second signal; and providing said first signal and said second signal to said receiving computing electronics; and computing at least one difference between said first signal and said second signal.

In another aspect, a super resolution system, the system comprising: at least one antenna; transmission electronics; receiving electronics; and receiving computing electronics, wherein said transmission electronics are structured to transmit a first electromagnetic wave having an Orbital Angular Momentum wave-front thru said antenna towards a target, wherein said transmission electronics are structured to transmit a second electromagnetic wave having a non Orbital Angular Momentum wave-front thru a first portion of said antenna towards said target, wherein said receiving electronics are structured to form a first signal from a first return wave of said first electromagnetic wave, wherein said receiving electronics are structured to form a second signal from a second return wave of said second electromagnetic wave, and wherein said receiving computing electronics are structured to compute target information by using at least one difference between said first signal and said second signal.

In another aspect, a super resolution system, the system comprising: at least one antenna; transmission electronics; receiving electronics; and receiving computing electronics, wherein said transmission electronics are structured to transmit a first electromagnetic wave having a non Orbital Angular Momentum wave-front thru a first portion of said antenna towards a target, wherein said transmission electronics are structured to transmit a second electromagnetic wave having an Orbital Angular Momentum wave-front thru said antenna towards said target, wherein said receiving electronics are structured to form a first signal from a first return wave of said first electromagnetic wave, wherein said receiving electronics are structured to form a second signal from a second return wave of said second electromagnetic wave, and wherein said receiving computing electronics are structured to compute target information by using at least one difference between said first signal and said second signal.

In another aspect, a method for operating a super resolution system, the method comprising: providing a super resolution system comprising at least one antenna, transmission electronics, receiving electronics, and receiving computing electronics; forming a first electromagnetic wave comprising an Orbital Angular Momentum wave-front, wherein said transmission electronics are used to form said first electromagnetic wave; transmitting said first electromagnetic wave using said antenna; forming a second electromagnetic wave comprising a non Orbital Angular Momentum wave-front, wherein said transmission electronics are used to form said second electromagnetic wave; transmitting said second electromagnetic wave using a first portion of said antenna; receiving a first return wave comprising said first electromagnetic wave; processing said first return wave to form a first signal; receiving a second return wave comprising said second electromagnetic wave; processing said second return wave to form a second signal; and providing said first signal and said second signal to said receiving computing electronics; and computing at least one difference between said first signal and said second signal.

In another aspect, an electromagnetic wave medical imaging system, the system including: at least one antenna; transmission electronics; receiving electronics; and receiving computing electronics, where the transmission electronics are structured to transmit a first electromagnetic wave having an Orbital Angular Momentum wave-front thru the antenna towards a target, where the transmission electronics are structured to transmit a second electromagnetic wave having a non Orbital Angular Momentum wave-front thru a first portion of the antenna towards the target, where the receiving electronics are structured to form a first signal from a first return wave of the first electromagnetic wave, where the receiving electronics are structured to form a second signal from a second return wave of the second electromagnetic wave, and where the system is designed to operate at a near field electromagnetic wave.

In another aspect, an electromagnetic wave medical imaging system, the system including: at least one antenna; transmission electronics; receiving electronics; and receiving computing electronics, where the transmission electronics are structured to transmit a first electromagnetic wave having a non Orbital Angular Momentum wave-front using the antenna towards a target, where the transmission electronics are structured to transmit a second electromagnetic wave having an Orbital Angular Momentum wave-front using the antenna towards the target, where the receiving electronics are structured to form a first signal from the first electromagnetic wave, where the receiving electronics are structured to form a second signal from the second electromagnetic wave, and where the receiving computing electronics are structured to compute target information by using at least one difference between the first signal and the second signal.

In another aspect, a method for operating a super resolution system, the method including: providing a super resolution system including at least one antenna, transmission electronics, receiving electronics, and receiving computing electronics; forming a first electromagnetic wave including an Orbital Angular Momentum wave-front, where the transmission electronics are used to form the first electromagnetic wave; transmitting the first electromagnetic wave using the antenna; forming a second electromagnetic wave including a non Orbital Angular Momentum wave-front, where the transmission electronics are used to form the second electromagnetic wave; transmitting the second electromagnetic wave using a first portion of the antenna; receiving a first wave resulted from the first electromagnetic wave; processing the first wave to form a first signal; receiving a second wave resulted from the second electromagnetic wave; processing the second wave to form a second signal; and providing the first signal and the second signal to the receiving computing electronics; and computing at least one difference between the first signal and the second signal.

BRIEF DESCRIPTION OF THE DRAWINGS

Various embodiments of the invention will be understood and appreciated more fully from the following detailed description, taken in conjunction with the drawings in which.

DETAILED DESCRIPTION

Figure 1A:
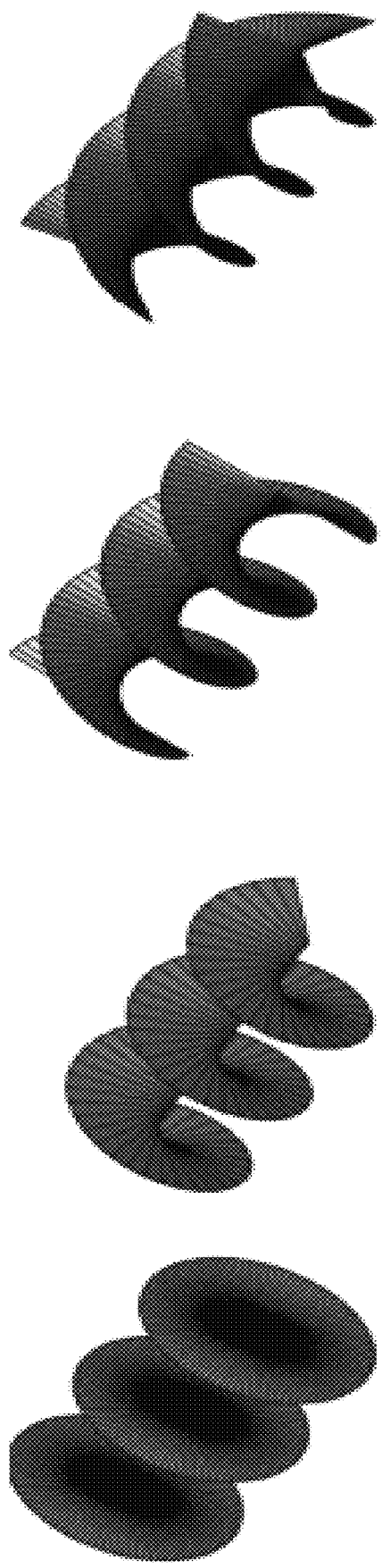
FIG. 1A is an example illustration of the wave front phase corresponding to OAM-modes 0, 1, 2, and 3.
Figure 1A:
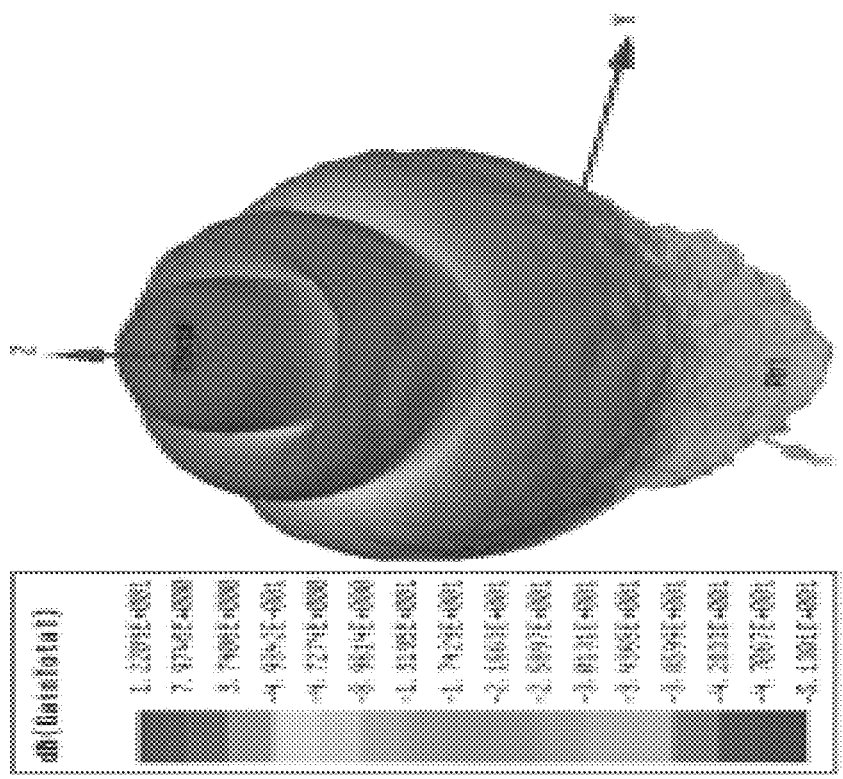
Figure 1A:
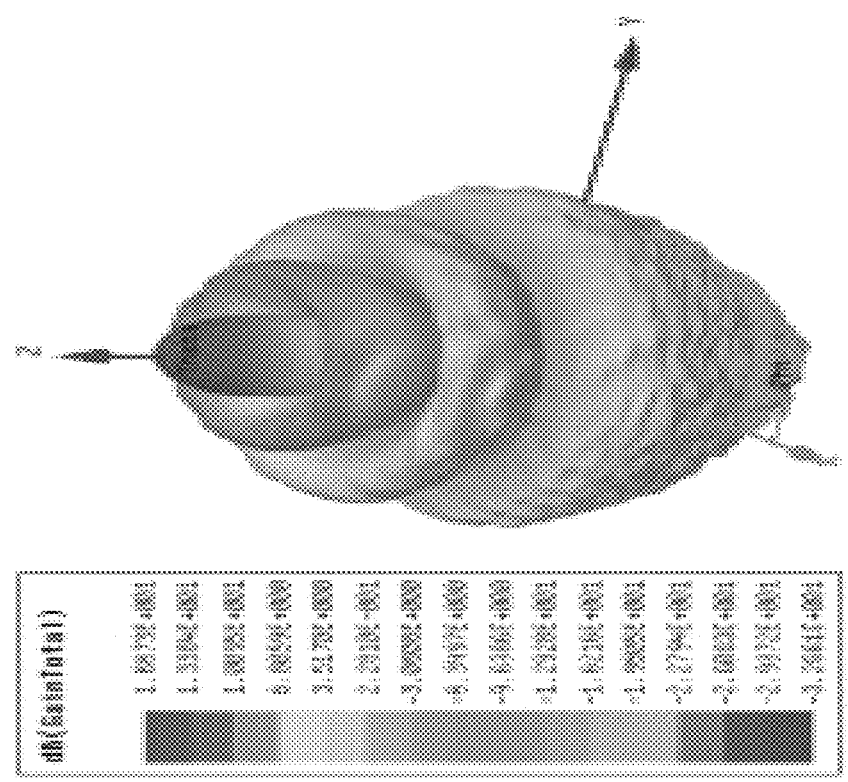
Figure 1A:
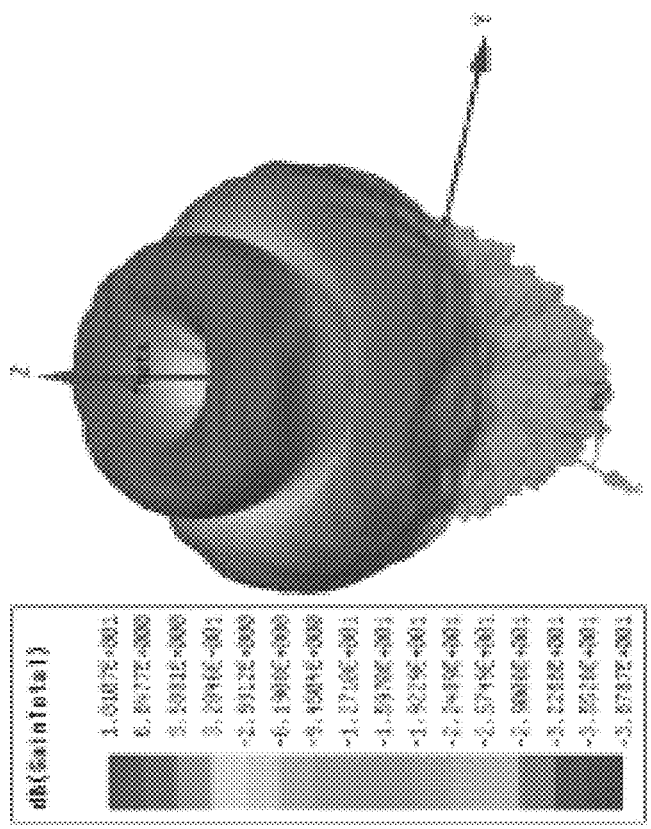
Figure 1A:
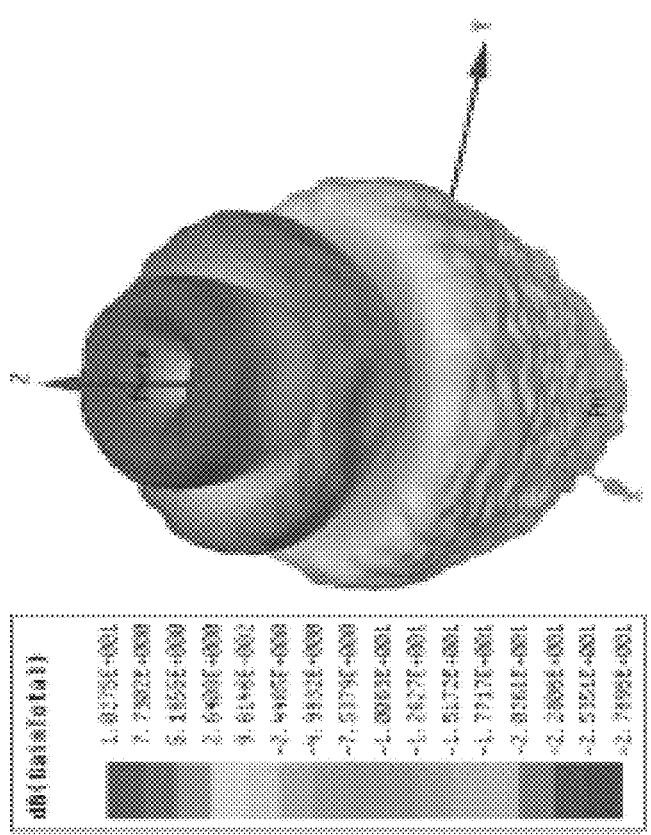
Figure 1B:
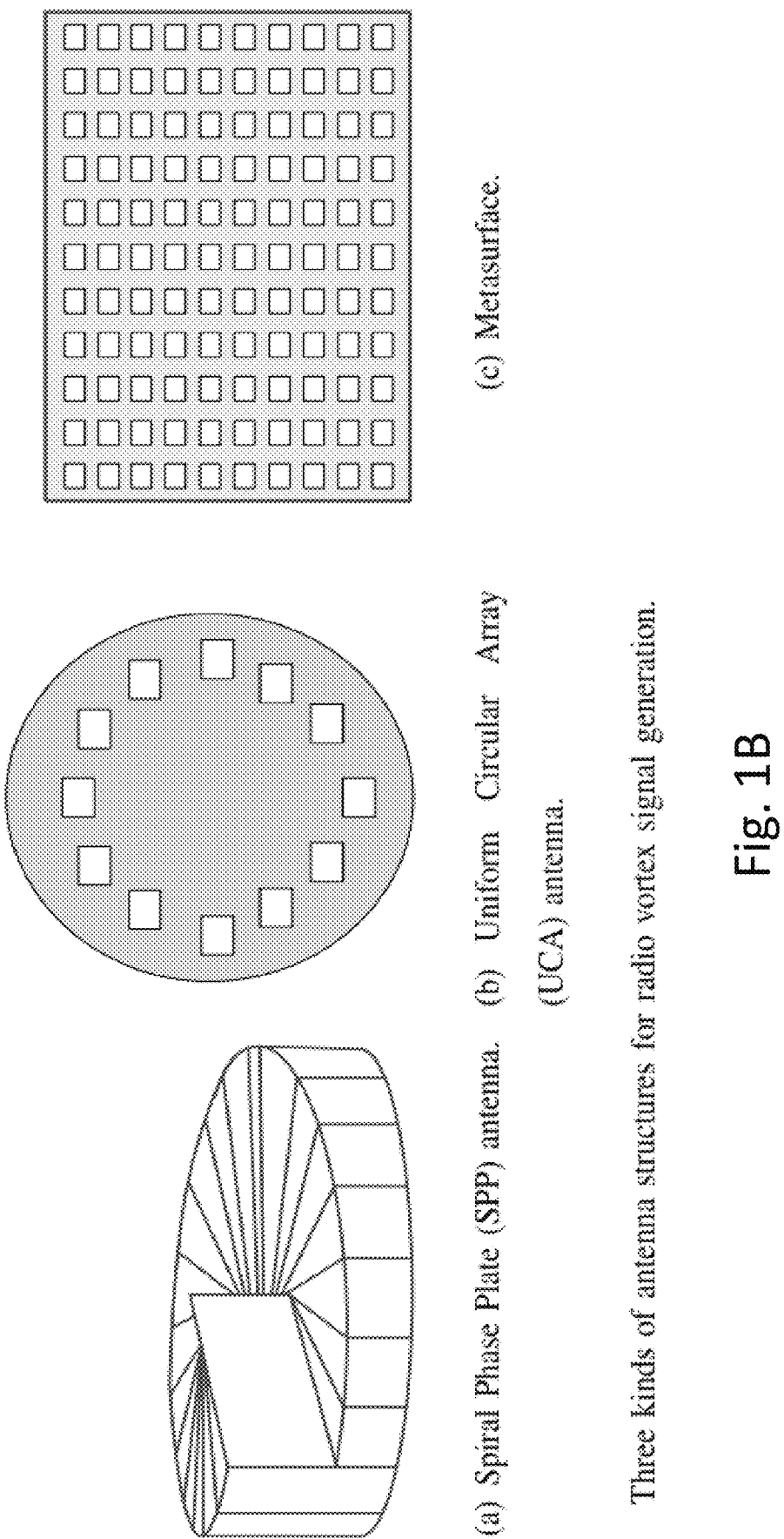
FIG. 1B is an example illustration of three kinds of antenna structures for radio vortex signal generation.

An embodiment of the invention is now described with reference to the drawing figures. Persons of ordinary skill in the art will appreciate that the description and figures illustrate rather than limit the invention and that in general the figures are not drawn to scale for clarity of presentation. Such skilled persons will also realize that many more embodiments are possible by applying the inventive principles contained herein and that such embodiments fall within the scope of the invention which is not to be limited except by any appended claims.

Figure 1C:
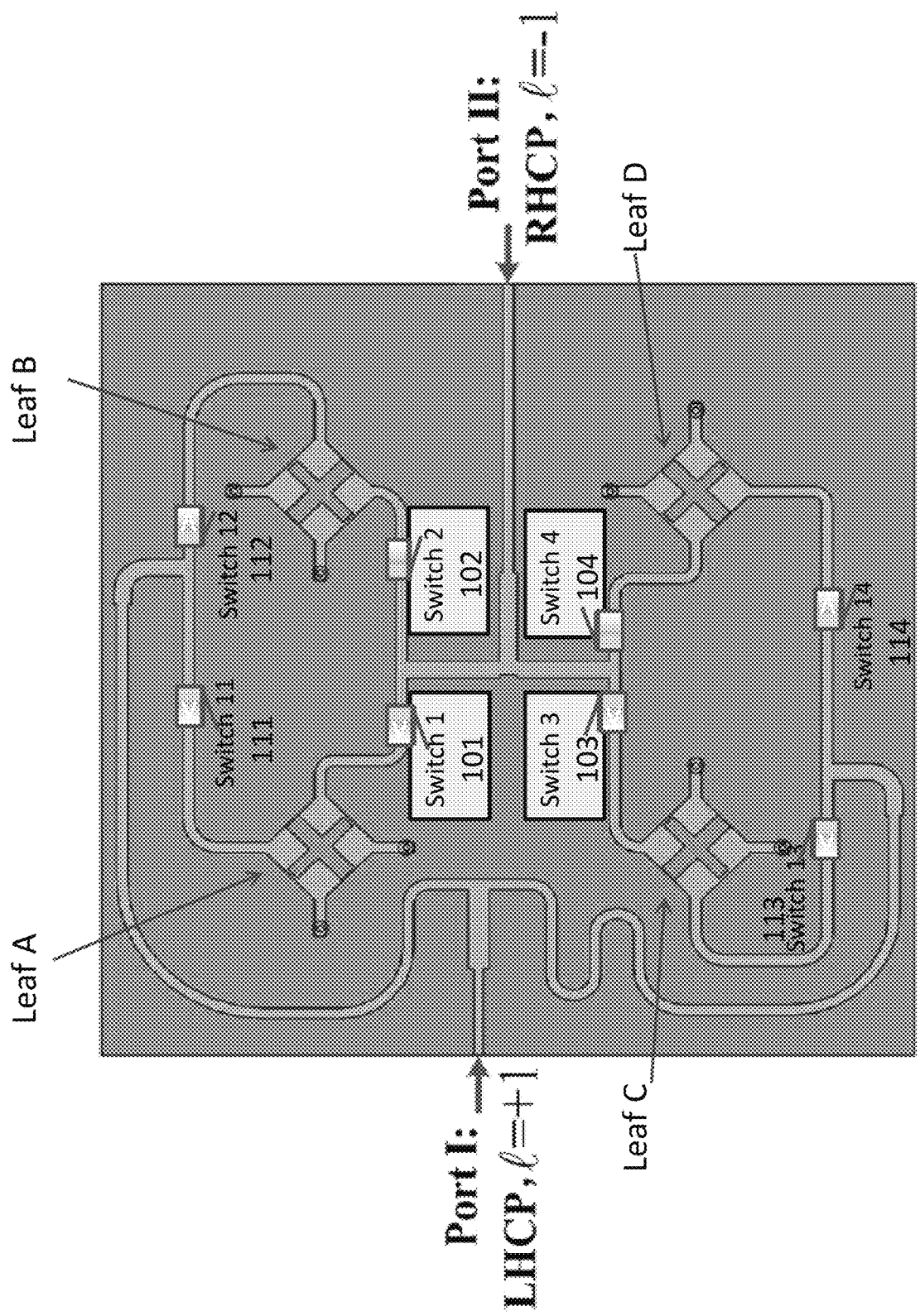
FIG. 1C is an example illustration of the functional transmitter's antenna array portion of the SRR.

FIG. 1C illustrates the antenna array of the functional transmitter portion of the SRR. In the paper by Bai, Xu-Dong, et al., "Experimental array for generating dual circularly-polarized dual-mode OAM radio beams." *Scientific reports* 7 (2017): an antenna array, typical four-element OAM-generating array is presented. FIG. 1C is the feeding structure of the antenna from the paper FIG. 2 (*e*). The presented antenna is designed to form OAM beam Right Handle Circular Polarization (RHCP) first order (1=−1) or Left Handle Circular Polarization (LHCP) 1=+1. For the application of SRR, four switches Switch-1 101, Switch-2 102, Switch-3 103, and Switch-4 104 are added to the feeding structure of Port II, and switches 111-114 (Switch-11 111, Switch-12 112, Switch-13 113, and Switch-14 114) are added to the feeding structure of Port I. These switches enable the cutting off or bypassing of each of the antenna leaves (Leaf A, leaf B, Leaf C, or Leaf D). When the switches are not active (normally on) the antenna would produce a Vortex beam RHCP 1=−1 or LHCP 1=+1 as detailed by the paper.

For the operation of SRR, EM beams are first projected with some of these switches active and accordingly the beams would have no singularity in its center. And then a beam with all switches switched on (conductive) is 'fired', thus producing a beam with a singularity at its center. The reflected EM containing the beam singularity is then compared to the return of the non-singular beam, with proper weight adjustment, producing a signal representing the return of the null region as all other returns are zeroed out. Such could be considered a self-alignment SRR as the same antenna is used to produce beams with a null in its vortex (singularity) and beams without a null in its vortex (non-singularity).

This concept could be applied with pulse RADAR in which each beam is fired for a short time. The concept could also be applied to supporting a continuous wave (CW), which is presented later herein.

The singular null in the center of an OAM beam is the product of the EM field in the very center being canceled out (overall destructive interference). By switching out at least one element (leaf) of the antenna, the null is voided and EM energy would be present in the vertex.

Such an SRR could include first pulsing a t1 ns pulse with interval of t2 ns, a beam from each of the leaves (by activating the proper switches) and then a pulse using all leaves—an OAM beam.

Figure 2:
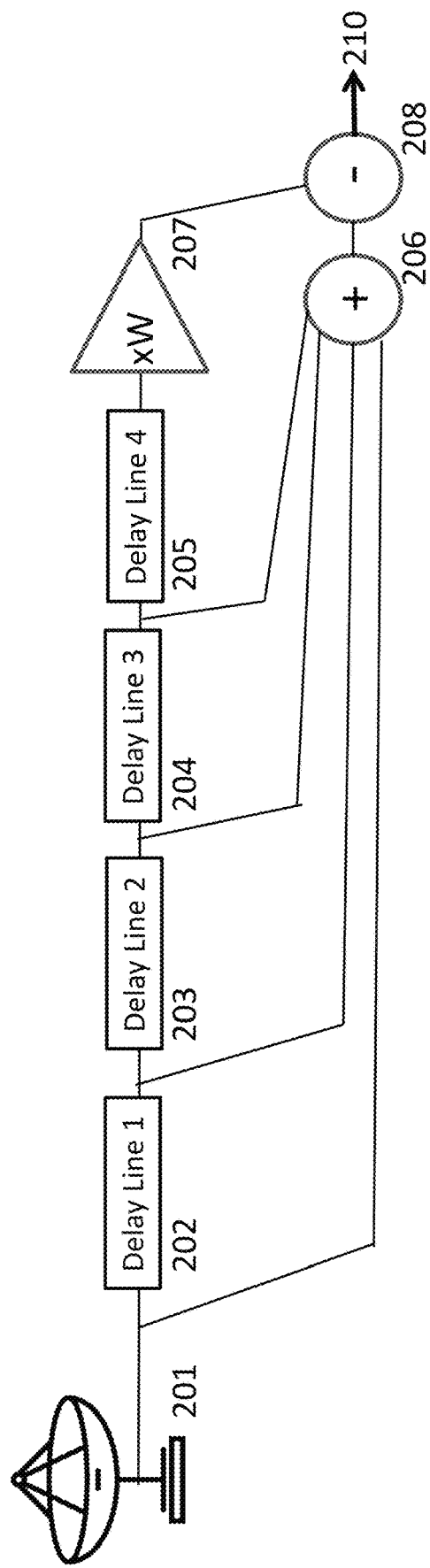
FIG. 2 is an example illustration of the functional receiver portion of the SRR.

FIG. 2 illustrates the functional receiver portion of the SRR. The signal collected by the Antenna array 201 may be processed by being fed into a sequence of four delay lines, delay line-1 202, delay line-2 203, delay line-3 204 and delay line-4 205, wherein each delay line is designed to delay the time between the pulses for t1+t2 ns. The output of the delay line-4 205 is fed to gain amplifier 207 designed to be amplified by the proper weight 'W' as compensation for the total energy of the four individual leaf pulses to follow. The four return signals from the four single leaf transmissions are summed by summing amplifier 206 and then have the amplified by 'W' return signal from the OAM signal (RHCP 1=−1 or LHCP 1=+1) first transmitted be subtracted from the sum using differential amplifier 208, thus forming the Super Resolution signal 210. Another alternative could be to mix the signal with the carrier frequency (down-convert) and then perform the processing at base-band. An energy detector could be used before the summation ("losing the phase").

Alternatively, the energy of the OAM pulse could be adjusted to reduce the need of the gain amplifier 207.

The circuits to implement the switches, the delay lines delay lines, the gain amplifier 207, the summation summing amplifier 206 and differential amplifier 208 could be engineered using circuits known in the art for an artisan in the RADAR and RF field. These circuits could also be integrated in an RF integrated IC such as RF-SOI. Other known in the RADAR art circuits could be integrated in the system before or after the elements illustrated in FIG. 1C and FIG. 2.

Another alternative is to use more than a single leaf for the beam without a null at the vertex. When more than a single leaf is used, a beam could include some level of singularity at its vertex. An SRR system could use a single delay line and generate sub-patterns by pulsing first an OAM beam and then a partial OAM beam, and then subtract forming a sub-pattern each time. Then those sub-patterns could be transferred for an image reconstruction computing system to resolve even more super resolution information from the subtracted return signals.

The concept could be applied with an antenna array that may have more than four elements (leaves). Some OAM antennas are constructed with an array of 16 elements or even more thus opening up a wide range of SRR system engineering using the presented concept.

Many other techniques of generating circular OAM EM waves are known in the art and the concept presented herein could be adapted for many of them. As an example, for such as is presented by Liu, Qiang, et al., "Circular Polarization and Mode Reconfigurable Wideband Orbital Angular Momentum Patch Array Antenna." *IEEE Transactions on Antennas and Propagation* 66.4 (2018): 1796-1804; by Deng, Changjiang, Kai Zhang, and Zhenghe Feng. "Generating and measuring tunable orbital angular momentum radio beams with digital control method." *IEEE Transactions on Antennas and Propagation* 65.2 (2017): 899-902; by Liu, Kang, et al., "Generation of OAM beams using phased array in the microwave band." *IEEE Transactions on Antennas and Propagation* 64.9 (2016): 3850-3857; by Liu, Dandan, et al., "Design and verification of monopole patch antenna systems to generate orbital angular momentum waves." *AIP Advances* 7.9 (2017): 095113; by Xi, Rui, Haixia Liu, and Long Li, "Generation and Analysis of High-Gain Orbital Angular Momentum Vortex Wave Using Circular Array and Parasitic EBG with oblique incidence." *Scientific reports* 7.1 (2017): 17363; by Bi, Fan, et al., "Dielectric Metasurface for Generating Broadband Millimeter Wave Orbital Angular Momentum Beams." *arXiv preprint arXiv:* 1801.06303 (2018); by Lee, Wangjoo, et al., "Microwave orbital angular momentum mode generation and multiplexing using a waveguide Butler matrix." *ETRI Journal* 39.3 (2017): 336-344; by Gong, Yinghui, et al., "Generation and transmission of OAM-carrying vortex beams using circular antenna array." *IEEE Transactions on Antennas and Propagation* 65.6 (2017): 2940-2949; by Sun, Chao, et al., "Realization of multiple orbital angular momentum modes simultaneously through four-dimensional antenna arrays." *Scientific reports* 8.1 (2018): 149; by Bai, Qiang, Alan Tennant, and Ben Allen, "Experimental circular phased array for generating OAM radio beams." *Electronics letters* 50.20 (2014): 1; by Cheng, Li, Wei Hong, and Zhang-Cheng Hao, "Generation of electromagnetic waves with arbitrary orbital angular momentum modes." *Scientific reports* 4 (2014): 4814; by Yu, Shixing, Long Li, and Guangming Shi, "Dual-polarization and dual-mode orbital angular momentum radio vortex beam generated by using reflective metasurface." *Applied Physics Express* 9.8 (2016): 082202; by Yu, Shixing, et al., "Design, fabrication, and measurement of reflective metasurface for orbital angular momentum vortex wave in radio frequency domain." *Applied Physics Letters* 108.12 (2016): 12190; by Mao, Fu-Chun, et al., "Orbital Angular Momentum Generation Using Circular Ring Resonators in Radio Frequency." *Chinese Physics Letters* 35.2 (2018): 02070; by Byun, Woo Jin, et al., "Multiplexed Cassegrain reflector antenna for simultaneous generation of three orbital angular momentum (OAM) modes." *Scientific reports* 6 (2016): 27339; by Yin, Jia Yuan, et al., "Microwave Vortex-Beam Emitter Based on Spoof Surface Plasmon Polaritons." *Laser & Photonics Reviews* 12.3 (2018): 1600316; by Jeong, Boseok, Hayeon Kim, and Haengseon Lee, "Indoor Propagation of Electromagnetic Waves with Orbital Angular Momentum at 5.8 GHz." *International Journal of Antennas and Propagation* 2018 (2018); by Wei, Wenlong, et al., "Generation of OAM waves with circular phase shifter and array of patch antennas." *Electronics letters* 51.6 (2015): 442-443; by Ren, Jian, and Kwok Wa Leung, "Generation of High-Purity Millimeter-Wave Orbital Angular Momentum Modes Using Horn Antenna: Theory and Implementation." *arXiv preprint arXiv:* 1710.00035 (2017); Yang, Tianming, et al. "Experimentally Validated, Wideband, Compact, OAM Antennas Based on Circular Vivaldi Antenna Array." *Progress In Electromagnetics Research* 80 (2018): 211-219; by Rajan, S. Palanivel, and M. Poovizhi, "Design of Patch Antenna Array for Radar Communication." *Journal of Chemical and Pharmaceutical Sciences, ISSN* 0974-2115 (2016): 38-40; by Fang, Lei, Haohan Yao, and Rashaunda Henderson, "Design and performance of OAM modes generated using dipole arrays with different feeds." *Radio and Wireless Symposium (RWS)*, 2018 *IEEE*. IEEE, 2018; by Nguyen, Tung, et al., "A study of orbital angular momentum generated by parabolic reflector with circular array feed." *Antennas and Propagation (ISAP)*, 2016 *International Symposium on*. IEEE, 2016; by Jiang, Shan, et al., "Achromatic electromagnetic metasurface for generating a vortex wave with orbital angular momentum (OAM)." *Optics express* 26.5 (2018): 6466-6477; and Liu, Kang, et al., "Radiation pattern control and synthesis for the generation of OAM-beams." *Progress in Electromagnetic Research Symposium (PIERS)*. IEEE, 2016, all of the foregoing are incorporated herein by reference.

The weight factor which could be used to amplify the reflected signal of the AOM wave could be adjusted based on the specific parameters of the antenna and the transmitting circuits. Such a gain adaptation could include a self-calibration mode in which the system first tunes the multiplying amplifier using a control target.

The SRR could be designed to operate for targets in the range of 20-200 meters with return signals being received at about 0.133 to 1.333 µs. For RADAR using a carrier of about 20 to 90 GHz, a pulse of about 10 ns (t1) and delay of about 10 ns (t2) could be used.

For a 200 m range the EM wave round trip delay is about 1.333 µs. For a 30 m range the EM wave, the round trip delay is about 0.2 µs. At 80 GHz a 10 ns pulse represents 800 oscillations.

These antennas could be configured to the desired modes. The switching between modes could utilize switches, for example, such as PIN Diodes, MEMs, Varactors, transistors or optical controls, as could be engineered for the specific applications and the specific frequency band of the application. These antennas could be designed for a single feed or multiple feeders. The switches could be part of the antenna forming structure and/or part of the signal conditioning. Some of these techniques are covered in a book by Semkin, Vasilii, "Reconfigurable antennas and radio wave propagation at millimeter-wave frequencies." (2016), incorporated herein by reference.

Another alternative is to transmit both OAM beam and non OAM beam with no interference in the center or partial interference, together yet at different frequencies. These frequencies could be chosen to be far enough apart so that the signal processing circuit could detect the return signal of each independent from the other, yet close enough so the same antenna could be used. This could enable continuous waves rather than pulse waves. Many types of antennas could be used for such a system. By engineering the antenna feeding structure the OAM beam could be at one frequency (f1), while the sub OAM beams could be other frequencies f2, f3, . . . .

Figure 3:
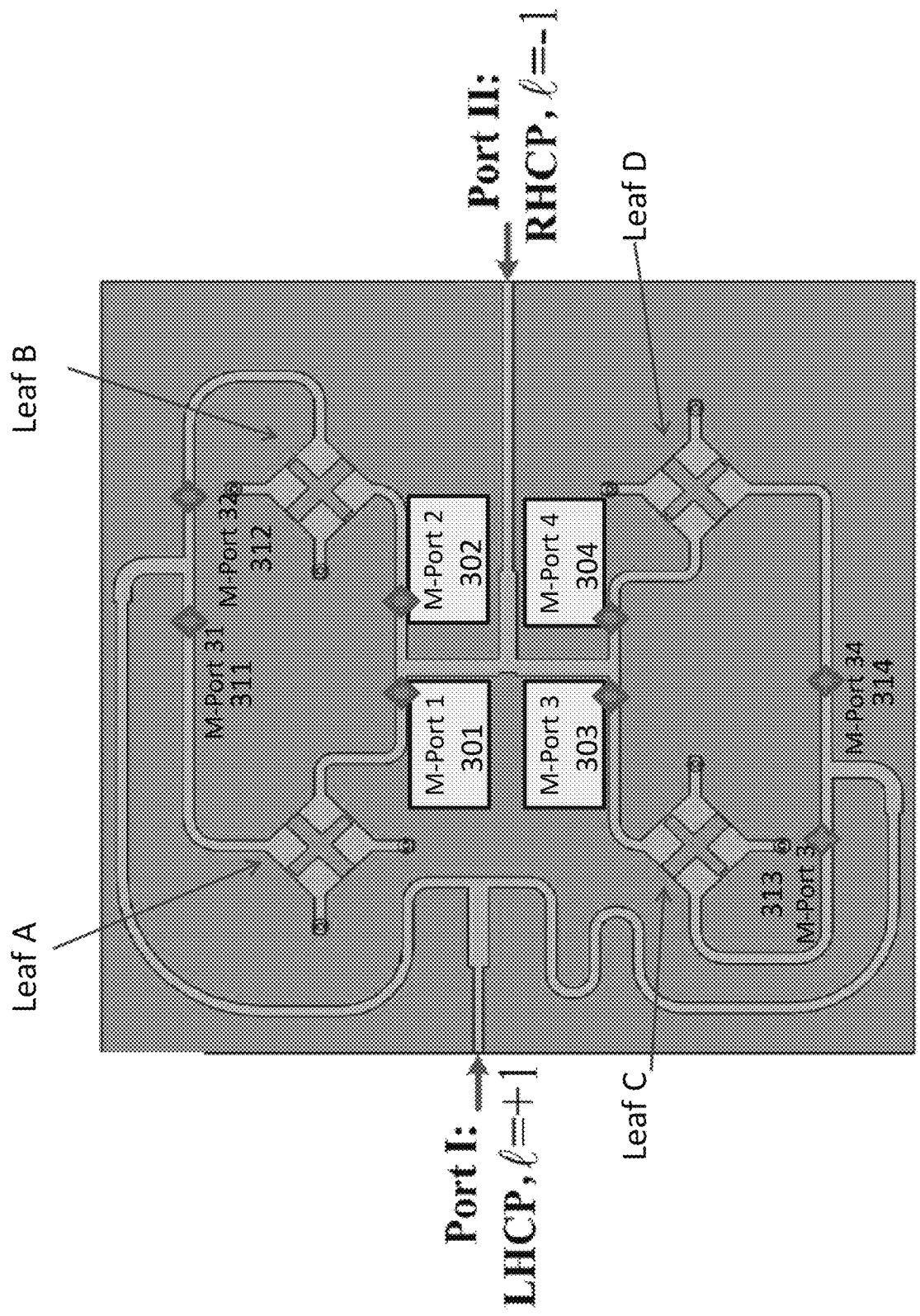
FIG. 3 is an example illustration of the functional transmitter's antenna array portion of the SRR.

FIG. 3 illustrates an example modification of the feeding structure illustrated in FIG. 1C. FIG. 3 illustrates replacing the switches with mixing ports (M-Port) 301-304 and 311-314. These mixing ports allow feed mixing in additional carrying waves to the individual leaf or a group of leaves.

The SRR could perform the following: Feed f1 carrying wave to Port I, sending out OAM (LHCP, l=+1) beam at f1, feeding f2 to Leaf A, feeding f3 to Leaf B, feeding f4 to Leaf C and f5 to Leaf D. The SRR could operate at CW where the target could be exposed to 5 beams (one with null at its center and the four others with conventional circular polarization beams). These five beams will generate five return signals: RS(f1), RS(f2), RS(f3), RS(f4), and RS(f5).

At the receiver, these return signals will be down converted by the front-end RF circuit to: rs(f1), rs(f2), rs(f3), rs(f4) and rs(f5). The SRR output signal could be processed to: SRR-Output=rs(f2)+rs(f3)+rs(f4)+rs(f5)−rs(f1)×W The engineering details of such system could be designed by an artisan in the RADAR art and could include many aspects including choice of the frequency band and the specific frequencies, the antenna, and the electronics for the transmit and receive subsystems.

This system as illustrated in FIG. 3 could also be used in a pulse mode. Much of the signal processing techniques used for RADAR could also be used for SRR including, for example, range measurements, speed measurements and so forth.

In many applications the reflected signal such as rs(f1) could be used to obtain general target data. In such respect it could be used like our eyes in which we get lower resolution peripheral vision and higher resolution in the center.

Alternatively, for applications in which the target has no polarity sensitivity it might be enough to use just one leaf such as RS(f2), and adjust the weight W accordingly.

Another alternative is to use more than one antenna in close proximity. As the size of the antenna could be at one or few centimeters while the target could be tens of meter far, it could be effective for some applications to use one antenna and driving electronics for OAM, another for the four leaves (Leaf A, B, C, D). These antennas could be made very similar (using the same patterns) and placed in very close proximity, for example, less than about 1 cm, or less than about 1 mm, or less than about 10 microns.

The adjustment of the weight W could include a self-test mode for improved adjustment. Such a self-test could use a designated scene, or even add in a blocking structure to block the center of the transmitted beam. If the beam center is blocked then the weight W could be set so that it minimizes the average RSS output signal during such a self-calibration step.

In some applications it could be desired to use an elliptical vertex instead of circular vertex. This could degrade somewhat the SRR resolution but could better fit the specific application needs. Alternatively the RSS could use other orders of OAM such l=+2 and so forth.

In some applications it could be desired to reduce signal to noise. A common technique is to perform multiple samplings and then average out the noise. Such could be enhanced by repeating the measurement with other orders of the OAM beam such as l=+1, l=−1, l=+2, l=−2, . . . .

An additional alternative is to transmit two OAM beams such as—RHCP, LHCP and sum them (either at the EM field) or at the return signal stage. And then subtract the return from the return of X-LP (Assuming that X is the orientation of the linear polarization field resulted from the summation of RHCP, LHCP.).

An additional alternative for noise reduction using averaging is to sample at different carrier frequencies including alternating frequencies between OAM beam and non-OAM beam or sub-OAM beams, and average the noise out.

An additional alternative is constructing an SRR system that obtains a higher level of information for the region covered by the null of the OAM beam. In such a system the subtraction is not from a return signal off a beam that has no interference in its vortex but rather from a beam that has partial interference in its vortex.

For example, using the relatively simple antenna of FIG. 3 with just 4 elements the system could generate multiple sub-return signals such as:
  Sub-AB=return from beam of Leaf A and Leaf B
  Sub-AC=return from beam of Leaf A and Leaf C
  Sub-AD=return from beam of Leaf A and Leaf D
  Sub-BC=return from beam of Leaf B and Leaf C
  Sub-BD=return from beam of Leaf B and Leaf D
  Sub-CD=return from beam of Leaf C and Leaf D
  Sub-ABC=return from beam of Leaf A and Leaf B and Leaf C
  Sub-ABD=return from beam of Leaf A and Leaf B and Leaf D
  Sub-ACD=return from beam of Leaf A and Leaf C and Leaf D
  Sub-BCD=return from beam of Leaf B and Leaf C and Leaf D
Each of these sub-returns could be subtracted by a properly weighted OAM return to form multiple sub-output signals which then could be fed into a reconstruction process to form the final SRR output.

In some applications and especially when the return signal is not affected by the beam polarity some of these sub-returns are about the same as other sub-returns, such as when Sub-AB is much like Sub-BC and those could be pruned down.

An additional alternative is to use an antenna with more elements and accordingly use many more=Sub-Returns signals to enable an even higher level of super resolution target reconstruction.

In other applications and especially for targets for which a return signal is sensitive to the polarity of the wave, the return of a beam from by transmitting wave out of one antenna element such as A could be different than the return from transmitting wave out of another antenna element such as B, and capturing and processing these variations could enable an improved target reconstruction.

An additional alternative is to leverage the fact that the "The central hollow (also called herein as null) increases as the order of OAM-mode increases", as is illustrated in FIG. 1A (f) to (h). Accordingly the concept presented herein for SRR by subtracting a non OAM or sub OAM return signal with the OAM return signal could be extended for subtracting the return signal of an OAM wave of higher OAM-mode (1=+2, 1=+3, . . . ) and sub-OAM of higher OAM-mode, generating sub-resolution info of the zones surrounding the null zone of OAM-mode 1=+1. These additional SRR variations could be engineered to support specific implementation of SRR system. Many of the techniques presented herein with respect to 1=+1 node could be extended accordingly.

The SRR system may include structures or techniques known in the art of RADAR and radio system to focus the beam and to reduce beam divergence. As the OAM beam had attracted attention for improved spectrum efficiency for wire-less communication such techniques had been recently developed and adapted to OAM type beams. Such are detailed in at least U.S. patents and applications, U.S. Pat. Nos. 9,413,448, 2016/0044647, 2016/0359539, 2017/0230115, and at least in papers such as: Cheng, Wenchi, et al., "Orbital-angular-momentum embedded massive MIMO: Achieving multiplicative spectrum-efficiency for mmWave communications." *IEEE Access* 6 (2018): 2732-2745; by Zhang, Kuang, et al., "Phase-engineered metalenses to generate converging and non-diffractive vortex beam carrying orbital angular momentum in microwave region." *Optics express* 26.2 (2018): 1351-1360; by Qin, Yuliang, et al., "Sidelobe suppression and beam collimation in the generation of vortex electromagnetic waves for radar imaging." *IEEE Antennas and Wireless Propagation Letters* 16 (2017): 1289-1292; by Ding, Guowen, et al., "Full control of conical beam carrying orbital angular momentum by reflective metasurface." *Optics Express* 26.16 (2018): 20990-21002, and by techniques known as Airy OAM Beams such as presented in a paper by Kadlimatti, Ravi, and Patanjali V. Parimi. "Millimeter-wave nondiffracting circular airy OAM beams." *IEEE Transactions on Antennas and Propagation* 67.1 (2018): 260-269; by Liu, Changming, et al., "Terahertz circular Airy vortex beams." *Scientific reports* 7.1 (2017): 3891; by Yan, Xu, et al., "Probability density of orbital angular momentum mode of autofocusing Airy beam carrying power-exponent-phase vortex through weak anisotropic atmosphere turbulence." *Optics express* 25.13 (2017): 15286-15298; and by Kadlimatti, Ravi, et al., "Wideband mm-wave non-diffracting Airy beam forming." (2018): 309-5, all of the foregoing are incorporated herein by reference.

An additional technique to reduce the effect of reflections from other objects is time control. The SRR could include signal processing to filter out or ignore return waves that do not meet the expected travel time to the target and back. These techniques are common in the RADAR art and could be implemented with pulse RADAR and even with CW RADAR.

The SRR could include a scanning mechanization for the formation of line (1D) or area (2D) image of the target. Many scanning mechanisms are known in the art including use of Galvo or other type of motors. These could be designed by an artisan in the art. An additional alternative is to use an antenna structure and support electronics that enable 1D or 2D scanning. Some of those utilize an array of small antennas, also known as 'phased array'. Some of these scanning techniques are covered in publications such as: Zhao, Zhe, et al., "Performance of Using Antenna Arrays to Generate and Receive mm-Wave Orbital-Angular-Momentum Beams." *GLOBECOM 2017-2017IEEE Global Communications Conference.* IEEE, 2017; by Lin, Mingtuan, et al., "Performance Analyses of the Radio Orbital Angular Momentum Steering Technique Based on Ka-Band Antenna." *International Journal of Antennas and Propagation* 2017 (2017); by Song, Qilong, et al., "Beam steering for OAM beams using time-modulated circular arrays." *Electronics Letters* (2018); and by Yu, Shixing, et al., "Generating multiple orbital angular momentum vortex beams using a metasurface in radio frequency domain." *Applied Physics Letters* 108.24 (2016): 241901, all of the foregoing are incorporated herein by reference. An artisan in the RADAR art can integrate the SRR concept presented herein with such a RADAR scanning technology to construct an imaging RADAR Super Resolution system.

The SRR technology could be used for common RADAR applications by enabling the use of lower frequencies and compensate for the resolution penalties by using the presented Super Resolution technology herein. Lower frequencies would enable either a longer range or lower RADAR energy as path loss is dramatically reduced for lower frequencies.

SRR combined with a scanning technology could be used to construct Super Resolution Imaging RADAR System—SRIRS. SRIRS and SRIRS derivatives could be used for many known RADAR applications and also could extend the use of Electro-Magnetic (EM) waves to other imaging applications, including medical imaging applications.

For medical imaging, SRIRS could be very attractive as its use of low energy EM waves relieves the patient's and operator's concern from the radiation effects associated with X-ray and other medical imaging technologies. SRIRS could also be built at a far lower cost and could allow real time imaging. Such could open up many medical imaging opportunities that due to the low resolution of conventional EM technologies were less aggressively investigated. In a review paper: Chandra, Rohit, et al., "On the opportunities and challenges in microwave medical sensing and imaging." *IEEE transactions on biomedical engineering* 62.7 (2015): 1667-1682, incorporated herein by reference, many applications of EM waves for medical imaging are reviewed. Quoting from the paper summary: "though the MSI ('Microwave sensing and imaging') system has advantages such as low risk, mobility, time resolution, and cost effectiveness, it lacks especially in spatial resolution compared to CT or MRI." Using the SRIRS as presented herein could enable the overcoming of such a deficiency and open the use of EM waves for many medical applications. An additional advantage is related to another aspect discussed in the paper, quoting from the paper: "penetration depth decreases with the frequency due to increased attenuation in the tissues, however, the resolution increases with the frequency." Accordingly use of SRIRS could allow a lower carrier wave frequency for deeper penetration while using the SRIRS could provide the required spatial resolution. An additional review of Microwave for Medical imaging is provided in a paper Hagness, Susan C., Elise C. Fear, and Andrea Massa, "Guest editorial: special cluster on microwave medical imaging." *IEEE Antennas and wireless propagation letters* 11 (2012): 1592-1597; and by Fasoula, Angie, et al., "Microwave vision: From RF safety to medical imaging." *Antennas and Propagation (EUCAP)*, 2017 11*th European Conference on.* IEEE, 2017, both incorporated herein by reference.

The imaging system utilizing SRIRS could utilize the reflective wave and/or transmission wave through the body under imaging. It could utilize multiple receiving antennas to analyze the EM wave interaction with the body under imaging.

It could be constructed in a conventional Computerize Tomography (CT) manner at least similar to the concept presented in the paper: Jofre, Luis, et al., "Medical imaging with a microwave tomographic scanner." *IEEE Transactions on Biomedical Engineering* 37.3 (1990): 303-312; and by Semenov, Serguei Y., and Douglas R. Corfield, "Microwave tomography for brain imaging: Feasibility assessment for stroke detection." *International Journal of Antennas and Propagation* 2008 (2008), both incorporated herein by reference.

Microwave medical imaging could be performed using EM pulses or continuous waves as could be engineered by an artisan in RADAR for medical imaging. The high pulse rate available in such a RADAR opportunity will open many new medical imaging opportunities. In such a system it might be desired to perform real time imaging of a patient. It might be desired to provide electronic image stabilization by compensating for target movement. The movement information could be provided by an attached conventional imager such as a video camera, or by information of the RADAR signal before the subtraction process for the super resolution information.

For medical imaging the frequency range of 1 GHz to 10 GHz is preferred as at these frequencies the penetration depth into the human body by radio waves is still very reasonable. Such a frequency range is associated with wavelength of 3 cm to 30 cm which could represent operation in "near field". Many of the wave form generation techniques previously presented would form an OAM wave in the near field as well. An important advantage in medical imaging for SRR is the minimal divergence of the EM waves at the near field. Minimal wave divergence in the near field could be also be important for high bandwidth communication system seeking to leverage the many modes of beams associated with OAM for bandwidth extension. In such communication systems, the minimal divergence helps to keep the size of the receiver antenna reasonable.

Multiple papers have reported forming OAM waves and measuring them in near field showing high quality OAM waves at the near field such as, a paper by Akram, Muhammad Rizwan, Liangqi Gui, and Dandan Liu. "OAM radio waves generation using dielectric resonator antenna array." 2016 *Asia-Pacific International Symposium on Electromagnetic Compatibility (APEMC)*. Vol. 1. IEEE, 2016; by Liu, Baiyang, et al. "An orbital angular momentum (OAM) mode reconfigurable antenna for channel capacity improvement and digital data encoding." *Scientific reports* 7.1 (2017): 1-9; by Bai, Xu-Dong, et al. "Experimental array for generating dual circularly-polarized dual-mode OAM radio beams." *Scientific reports* 7.1 (2017): 1-8; by Spinello, Fabio, et al. "Experimental near field OAM-based communication with circular patch array." *arXiv preprint arXiv:* 1507.06889 (2015); by Liu, Dandan, et al. "Design and verification of monopole patch antenna systems to generate orbital angular momentum waves." *AIP Advances* 7.9 (2017): 095113; by Assimonis, Stylianos D., Muhammad Ali Babar Abbasi, and Vincent Fusco. "Millimeter-wave multi-mode circular antenna array for uni-cast multi-cast and OAM communication." *Scientific Reports* 11.1 (2021): 1-11; by Zhao, Zhe, et al. "Performance of using antenna arrays to generate and receive mm-wave orbital-angular-momentum beams." *GLOBECOM* 2017-2017 *IEEE Global Communications Conference*. IEEE, 2017; by Gong, Yinghui, et al. "Generation and transmission of OAM-carrying vortex beams using circular antenna array." *IEEE Transactions on antennas and propagation* 65.6 (2017): 2940-2949; and by Shao, Wenyi, and Todd McCollough. "Advances in microwave near-field imaging: Prototypes, systems, and applications." IEEE microwave magazine 21.5 (2020): 94-119, all of the foregoing are incorporated herein by reference. These papers present and validate systems including antennas that are relatively simple and compact to generated OAM waves at lease for mode 1 (and −1) having proven OAM waves in the near field and could be useful as part of SRR system for medical imaging using techniques previously presented herein. In these system the vertex/null size could be well below 1 mm which according the techniques previously presented here and by adding scanning options—SRIRS—could be used to construct a medical imaging system using radio waves at the range of 1 GHz to 10 GHz providing an image resolution of less than 1 mm.

Lack of resolution is considered the main reason that radio waves are not common in the field of medical imaging. There are indication that radio waves are getting close to commercial use for breast cancer and head scanning application as presented in paper by Kuwahara, Yoshihiko, and A. M. Malik. "Microwave imaging for early breast cancer detection." *New Perspect. Breast Imaging* (2017): 45-71; and by Wang, Dang-Dang, et al. "A new method for transcranial vortex microwave beam imaging." 2018 *International Conference on Microwave and Millimeter Wave Technology (ICMMT)*. IEEE, 2018, both are incorporated herein by reference.

To reduce reflection and for better matching of the antenna and the human body, some references suggest to use water as an interface media such as presented in a paper by Yang, Y. A. N. G., et al. "Study of a water-immersed orbital angular momentum circular antenna array." 2018 *IEEE International Symposium on Antennas and Propagation & USNC/URSI National Radio Science Meeting*. IEEE, 2018, incorporated herein by reference.

The receiver signal processing could be simple as is illustrated in FIG. 2 but could be done using computing technology. The antenna modeling technology could predict the electromagnetic wave generation at good fidelity compared to the actual wave. The computer could compare the received signal of the non OAM signal as could be generated by each of the antenna elements to the return wave of the OAM signal as is generated by all the antenna elements generating the OAM wave. Since the target is the same and the antenna is well characterized, the computer can compute the data associated with the target elements that will not be reflecting since they are at the OAM vertex and accordingly have not been receiving electromagnetic waves when OAM waves were generated and transmitted to the target. Using scanning a full target high resolution image could be reconstructed.

Figure 4A:
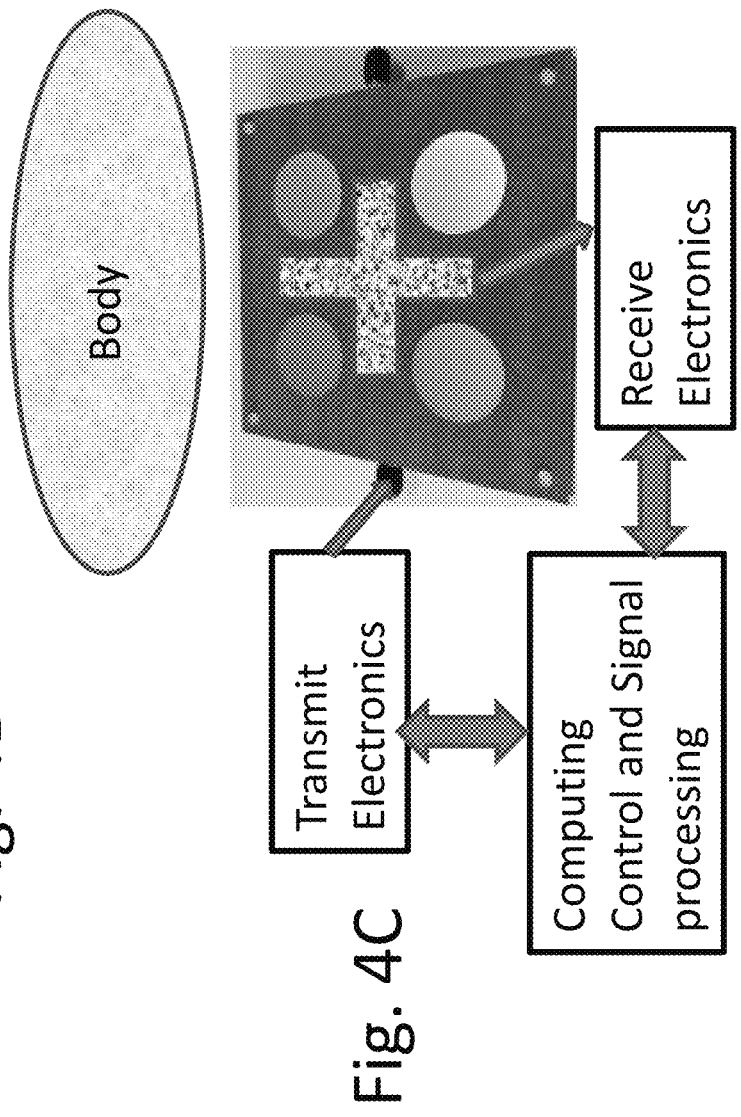
FIG. 4A is an example illustration of a four element circular array designed to generate OAM waves.

FIG. 4A illustrates a four element circular array designed to generate OAM wave is detailed in the paper by Bai, Xu-Dong, et al. "Experimental array for generating dual circularly-polarized dual-mode OAM radio beams." *Scientific reports* 7.1 (2017): 1-8.

Figure 4B:
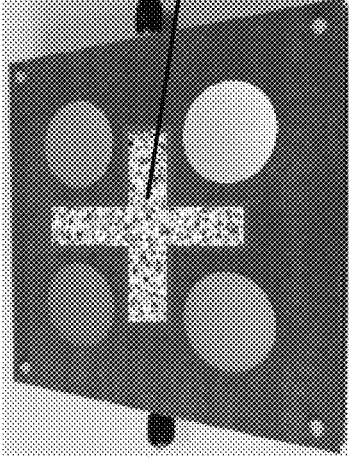
FIG. 4B is an example illustration of an OAM generating antenna with additionally a signal receiving antenna.

FIG. 4B illustrates the OAM generating antenna 402 with an additional signal receiving antenna 404.

Figure 4C:
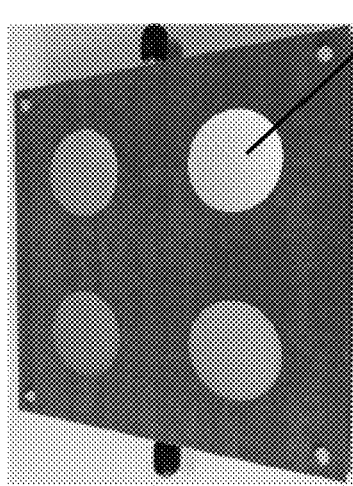
FIG. 4C is an example illustration of a medical imaging OAM RADAR system using a transmitting antenna and receiving antenna.

FIG. 4C illustrates a medical imaging OAM RADAR system using transmitting antenna 402 and receiving antenna 404. The system may include a computer which controls the Transmit Electronic and the Receive electronic. It could use the transmitting antenna 402 to send an OAM wave (or non OAM wave) toward the target which could be a part of a body and receive the signal to compute and form the image of the body being scanned. The target for medical imaging could be placed to receive the near field electromagnetic wave from the antenna.

The computer can calculate the difference between the signals received from a non OAM wave return to the signal received from the OAM wave return. The computer could adjust the date compensating some potential differences. The system could include self-adjusting steps including the use of calibrating with a synthetic target. The non OAM signal could be formed by using only one of the antenna elements at a time or using a slight different frequency to each of the antenna elements. The OAM signal is formed by using all the four elements with the same frequency but with proper phase shift forming an OAM wave with a singularity vertex having no energy (null) at the center of the wave.

The system could use a pulse of electromagnetic waves or modulated transmissions with signal recovery to measure the return at a specific penetration depth into the body.

In some systems the non OAM wave return from each of the elements are similar enough so the difference could be made by comparing the non OAM wave return of one element to the return of the four elements with fixed power compensation. In other systems it may be better to first capture some of the returns from each of the elements on their own and then compare to the return of the OAM wave. Post these compensation as the difference of the return are the attribute associated with the return of the body in the null zone which got no electromagnetic energy from the OAM wave.

The SRIRS could be designed to operate in real time and to be used to guide medical procedures in addition to conventional imaging. Various techniques could be used to enhance its operation. Many materials could be compatible with the subject under test's biology and have a good strong interaction with EM waves. Such EM imaging enhancement could replace similar techniques used for other types of imaging. Those could integrate with the medical apparatus use or be swallowed by the patient, injected in, and so forth. The specific spectrum used could be designed per the target application to match the target computability and the imaging objective.

An additional application of the SRR could be as replacement for use of a laser for range finding. Such as is used in a weapon, for example, tanks, fire control system. RADAR is very good for range finding but the relatively large beam had driven the use of the higher cost laser solution. With the SRR technology presented herein, an EM wave could be used effectively for range measurement. An additional advantage for SRR technology for such applications is the ability to avoid visually alarming the target at the measurement time.

An additional application of the SRR could be as a replacement for use of lasers for target pointers. Such as is used in a battle field to point targets by a front ground team marking targets for air-born munition guidance. SRR systems could be lighter, operate at lower energy and cost, than the use of the higher cost laser solution. With the SRR technology disclosed herein, an EM wave could be used effectively for range measurement. An additional advantage for SRR technology for such applications is the ability to avoid visually alarming the target during the time it is being marked.

Additional application use of SRIRS could be for night vision as an alternative to thermal imaging technology.

Additional application use of SRIRS could be for 3D imaging, leveraging the distance information available in a RADAR system.

Additional application use of SRIRS could be for through barrier imaging by an appropriate selection of the carrier frequency. EM waves at the proper frequency could penetrate walls and other barriers that block optical detection systems, leveraging the distance information available in a RADAR system, such an SRR based imaging system could be used to 'see' through barriers.

It will also be appreciated by persons of ordinary skill in the art that the invention is not limited to what has been particularly shown and described hereinabove. Rather, the scope of the invention includes combinations and sub-combinations of the various features described hereinabove as well as modifications and variations which would occur to such skilled persons upon reading the foregoing description. Thus the invention is to be limited only by any appended claims.

I claim:

1. An electromagnetic wave medical imaging system, the system comprising:
    at least one antenna;
    transmission electronics;
    receiving electronics; and
    receiving computing electronics,
        wherein said transmission electronics are structured to transmit a first electromagnetic wave having an Orbital Angular Momentum wave-front thru said antenna towards a target,
        wherein said transmission electronics are structured to transmit a second electromagnetic wave having a non Orbital Angular Momentum wave-front thru a first portion of said antenna towards said target,
        wherein said receiving electronics are structured to form a first signal from a first return wave of said first electromagnetic wave,
        wherein said receiving electronics are structured to form a second signal from a second return wave of said second electromagnetic wave, and
        wherein said system is designed to operate at a near field electromagnetic wave.

2. The system according to claim 1,
    wherein said antenna is a circular array type comprising at least four array elements.

3. The system according to claim 1,
    wherein said first electromagnetic wave has a first oscillating frequency and said second electromagnetic wave has a second oscillating frequency.

4. The system according to claim 1,
    wherein said first electromagnetic wave is transmitted at a first time interval, and said second electromagnetic wave is transmitted at a second time interval.

5. The system according to claim 1,
    wherein said transmission electronics are structured to transmit a third electromagnetic wave using a second portion of said antenna.

6. The system according to claim 1, further comprising:
    scanning electronics to support performing scanning of said target.

7. The system according to claim 1,
    wherein said receiving computing electronics are structured to compute target information by using at least one difference between said first signal and said second signal.

8. An electromagnetic wave medical imaging system, the system comprising:
    at least one antenna;
    transmission electronics;
    receiving electronics; and
    receiving computing electronics, wherein said transmission electronics are structured to transmit a first electromagnetic wave having a non Orbital Angular Momentum wave-front using said antenna towards a target,
wherein said transmission electronics are structured to transmit a second electromagnetic wave having an Orbital Angular Momentum wave-front using said antenna towards said target,
wherein said receiving electronics are structured to form a first signal from said first electromagnetic wave,
wherein said receiving electronics are structured to form a second signal from said second electromagnetic wave, and
wherein said receiving computing electronics are structured to compute target information by using at least one difference between said first signal and said second signal.

9. The system according to claim 8,
wherein said antenna is a circular array type comprising at least four array elements.

10. The system according to claim 8,
wherein said first electromagnetic wave has a first oscillating frequency and said second electromagnetic wave has a second oscillating frequency.

11. The system according to claim 8,
wherein said first electromagnetic wave is transmitted at a first time interval, and said second electromagnetic wave is transmitted at a second time interval.

12. The system according to claim 8,
wherein said antenna is a circular array type comprising at least four array elements,
wherein said second electromagnetic wave comprises use of at least said four array elements,
wherein said first electromagnetic wave comprises not using at least one of said antenna elements.

13. The system according to claim 8, further comprising:
scanning electronics to support performing scanning of said target.

14. The system according to claim 8,
wherein said receiving electronics are configured to receive return signals for said antenna to said target distances less of than 5 meters.

15. A method for operating a super resolution system, the method comprising:

providing a super resolution system comprising at least one antenna, transmission electronics, receiving electronics, and receiving computing electronics;
forming a first electromagnetic wave comprising an Orbital Angular Momentum wave-front,
wherein said transmission electronics are used to form said first electromagnetic wave;
transmitting said first electromagnetic wave using said antenna;
forming a second electromagnetic wave comprising a non Orbital Angular Momentum wave-front,
wherein said transmission electronics are used to form said second electromagnetic wave;
transmitting said second electromagnetic wave using a first portion of said antenna;
receiving a first wave resulted from said first electromagnetic wave;
processing said first wave to form a first signal;
receiving a second wave resulted from said second electromagnetic wave;
processing said second wave to form a second signal; and
providing said first signal and said second signal to said receiving computing electronics; and
computing at least one difference between said first signal and said second signal.

16. The method according to claim 15,
wherein said antenna is a circular array type comprising at least four array elements.

17. The method according to claim 15,
wherein said first electromagnetic wave comprises a first oscillating frequency and said second electromagnetic wave comprises a second oscillating frequency.

18. The method according to claim 15,
wherein said first electromagnetic wave is transmitted at a first time interval and said second electromagnetic wave is transmitted at a second time interval.

19. The method according to claim 15,
wherein said transmission electronics are structured to transmit a third electromagnetic wave thru a second portion of said antenna.

20. The method according to claim 15, further comprising:
performing a scan comprising space scanning electronics.

* * * * *